(12) United States Patent
Salemme et al.

(10) Patent No.: US 7,455,872 B2
(45) Date of Patent: *Nov. 25, 2008

(54) COMPOSITIONS AND METHODS FOR PRODUCING A SALTY TASTE IN FOODS OR BEVERAGES

(75) Inventors: Francis Raymond Salemme, Yardley, PA (US); Richard Barndt, Highland Park, NJ (US)

(73) Assignee: Redpoint Bio Corporation, Ewing, NJ (US)

( * ) Notice: Subject to any disclaimer, the term of this patent is extended or adjusted under 35 U.S.C. 154(b) by 510 days.

This patent is subject to a terminal disclaimer.

(21) Appl. No.: 11/155,745

(22) Filed: Jun. 20, 2005

(65) Prior Publication Data

US 2006/0286276 A1    Dec. 21, 2006

(51) Int. Cl.
*A23L 1/22* (2006.01)
*A23L 1/237* (2006.01)

(52) U.S. Cl. .................. 426/649; 426/74; 426/534; 426/535; 426/582; 426/590; 426/650

(58) Field of Classification Search ............ 426/649, 426/74, 534, 535, 582, 650, 590
See application file for complete search history.

(56) References Cited

U.S. PATENT DOCUMENTS

| | | |
|---|---|---|
| 3,505,082 A | 4/1970 | Miller |
| 3,647,482 A | 3/1972 | Yueh |
| 3,860,732 A | 1/1975 | Eisenstadt |
| 3,872,227 A | 3/1975 | Hoff et al. |
| 4,243,691 A | 1/1981 | Mohlenkamp, Jr. et al. |
| 4,297,375 A | 10/1981 | Shackelford |
| 4,376,132 A | 3/1983 | Eguchi et al. |
| T104,004 I4 | 3/1984 | von Rymon Lipinski |
| 4,514,431 A | 4/1985 | Buckhoz, Jr. et al. |
| 4,560,574 A | 12/1985 | Meyer |
| 4,563,359 A | 1/1986 | Shimizu et al. |
| 4,600,708 A | 7/1986 | Reuter et al. |
| 4,826,824 A | 5/1989 | Schiffman |
| 4,963,387 A | 10/1990 | Nakagawa et al. |
| 5,145,707 A | 9/1992 | Lee |
| 5,173,323 A | 12/1992 | Omari |
| 5,232,735 A | 8/1993 | Kurtz et al. |
| 5,372,834 A | 12/1994 | Buckholz, Jr. et al. |
| 5,589,357 A | 12/1996 | Martinez et al. |
| 5,631,038 A | 5/1997 | Kurtz et al. |
| 5,631,231 A | 5/1997 | Kurtz et al. |
| 5,631,232 A | 5/1997 | Kurtz et al. |
| 5,631,240 A | 5/1997 | Kurtz et al. |
| 5,631,252 A | 5/1997 | Kurtz et al. |
| 5,631,272 A | 5/1997 | Kurtz et al. |
| 5,631,292 A | 5/1997 | Kurtz et al. |
| 5,631,294 A | 5/1997 | Kurtz et al. |
| 5,631,295 A | 5/1997 | Kurtz et al. |
| 5,631,299 A | 5/1997 | Kurtz et al. |
| 5,637,618 A | 6/1997 | Kurtz et al. |
| 5,639,788 A | 6/1997 | Kurtz et al. |
| 5,641,795 A | 6/1997 | Kurtz et al. |
| 5,641,799 A | 6/1997 | Kurtz et al. |
| 5,641,811 A | 6/1997 | Kurtz et al. |
| 5,641,812 A | 6/1997 | Kurtz et al. |
| 5,643,894 A | 7/1997 | Kurtz et al. |
| 5,643,941 A | 7/1997 | Kurtz et al. |
| 5,643,945 A | 7/1997 | Kurtz et al. |
| 5,643,955 A | 7/1997 | Kurtz et al. |
| 5,643,956 A | 7/1997 | Kurtz et al. |
| 5,646,122 A | 7/1997 | Kurtz et al. |
| 5,650,403 A | 7/1997 | Kurtz et al. |
| 5,654,311 A | 8/1997 | Kurtz et al. |
| 5,665,755 A | 9/1997 | Kurtz et al. |
| 5,693,756 A | 12/1997 | Li et al. |
| 5,700,792 A | 12/1997 | Kurtz et al. |
| 5,703,053 A | 12/1997 | Kurtz et al. |
| 5,789,250 A | 8/1998 | Ikezaki |
| 5,817,759 A | 10/1998 | Margolskee |
| 5,853,792 A | 12/1998 | Zolotov et al. |
| 5,866,608 A | 2/1999 | Kurtz et al. |
| 5,897,908 A | 4/1999 | Berglund et al. |
| 6,008,250 A | 12/1999 | Kurtz et al. |
| 6,015,792 A | 1/2000 | Kurtz et al. |
| 6,368,651 B1 | 4/2002 | Gerlat et al. |
| 6,540,978 B1 | 4/2003 | Margolskee et al. |
| 6,541,050 B1 | 4/2003 | Bonorden et al. |
| 6,783,788 B2 | 8/2004 | Kuroda et al. |
| 6,942,874 B2 | 9/2005 | McGregor et al. |
| 2003/0035875 A1 | 2/2003 | Dulebohn et al. |
| 2003/0194423 A1 | 10/2003 | Torney et al. |

(Continued)

FOREIGN PATENT DOCUMENTS

CH      497 136 A    11/1970

(Continued)

OTHER PUBLICATIONS

RD 20729, Jul. 10, 1981, Anonymous.
Anderson, J., et al., "Potassium and Health," Colorado State University Cooperative Extension, last updated on Apr. 8, 2005, accessed online at http://www.ext.colostate.edu/pubs/foodnut/09355.html on May 15, 2005, pp. 1-4.
Chiou, T.-K. and Lai, M.-M., "Comparison of taste components in cooked meats of small abalone fed different diets," *Fisheries Science* 68:388-394, Blackwell Publishing (2002).

(Continued)

*Primary Examiner*—Helen F Pratt
(74) *Attorney, Agent, or Firm*—Sterne, Kessler, Goldstein & Fox P.L.L.C.

(57) ABSTRACT

The present invention provides compositions containing bitterness inhibitors that reduce the bitter taste of KCl that is used in foods or beverages as a substitute for sodium chloride. The compositions contain as bitterness inhibitors taurine and 5'-adenosinic acid, and 5'-inosinic acid, and/or 5'-guanylic acid. Furthermore, the present invention provides methods of using these compositions and methods for preparing them.

49 Claims, No Drawings

FOREIGN PATENT DOCUMENTS

| | | |
|---|---|---|
| DE | 3331517 A1 | 3/1984 |
| EP | 0 059 363 B1 | 12/1984 |
| EP | 0 122 400 B1 | 7/1987 |
| EP | 0 125 021 B1 | 7/1987 |
| EP | 0 291 980 B1 | 1/1992 |
| EP | 0 416 667 B1 | 9/1993 |
| JP | 48-10227 | 4/1973 |
| JP | 48-17044 | 5/1973 |
| JP | 59-55165 A | 3/1984 |
| JP | 59-210866 A | 11/1984 |
| JP | 61-271969 A | 12/1986 |
| JP | 4-40881 A | 2/1992 |
| JP | 11-169131 A | 6/1999 |
| RU | 2003265 C1 | 11/1993 |
| WO | WO 97/04666 A1 | 2/1997 |
| WO | WO 00/38536 A2 | 7/2000 |
| WO | WO 02/096464 A1 | 12/2002 |
| WO | WO 03/075661 A1 | 9/2003 |

OTHER PUBLICATIONS

Chiou, T.-K., "Utilization of Cooking Waste of Canned Tuna As Flavorings," *Food Science* 208-217, The Chinese Institute of Food Science and Technology (1994).

Chiou, T.-K., et al., Seasonal variations of chemical constituents in the muscle and viscera of small abalone fed different diets, *Fisheries Science* 67:146-156, Blackwell Publishing (2001).

Communication from Quaker Foods & Beverages to the Food and Drug Administration Regarding Food Labeling; Nutrient Content Claims, Definition of Sodium Levels for the Term "Healthy" Docket Nos. 91N-384H and 96P-0500, pp. 1-4, mailed Jul. 10, 2003.

Danilova, V., et al., "Responses of Single Taste Fibers and Whole Chorda Tympani and Glossopharyngeal Nerve in the Domestic Pig, *Sus scrofa*," *Chem. Senses* 24:301-316, Oxford University Press (1999).

Unverified English language translation for CH 497 136 A, document FP1.

STN*Easy*/CAplus database, Accession No. 1974:36023, English language abstract for JP 48-10227, document FP 2.

STN/Easy CAplus database, Accession No. 1973:457692, English language abstract for JP 48-17044, document FP3.

Dialog File No. 351, Accession No. 3918294, Derwent WPI English language abstract for DE 3331517 A, FP5.

Dialog File No. 347, Accession No. 1343565, Derwent WPI English language abstract for JP 59-55165 A, document FP6.

Dialog File No. 347, Accession No. 1499266, Derwent WPI English language abstract for JP 59-210866 A, document FP7.

Dialog File No. 351, Accession No. 3529012, Derwent WPI English language abstract for EP 0 059 363 B1, document FP8.

STN*Easy*/CAplus database, Accession No. 1987:212816, English language abstract for JP 61-271969 A, document FP9.

Dialog File No. 351, Accession No. 8972382, Derwent WPI English language abstract for JP 4-40881 A, document FP13.

Dialog File No. 351, Accession No. 9810059, Derwent WPI English language abstract for RU 2003265 C, document FP15.

Japanese Patent Office, Patent Abstracts of Japan, English language abstract for 11-169131, document FP17.

Engel, E., et al., "Determination of taste-active compounds of a bitter Camembert cheese by omission tests," *J. Dairy Res.* 68:675-688, Cambridge University Press (2001).

"Flavor Potentiators," in *Flavor Chemistry and Technology*, Health, H.B. and Reineccius, G., eds., AVI Publishing Company, Inc. Westport Connecticut, pp. 318-331 (1986).

Fuke, S., "Taste-active components of seafoods with special reference to umami substances," in *Seafoods: Chemistry, Processing Technology and Quality*, 1st Ed., Shahidi, F. and Botta, J.R., eds., Chapman & Hall, pp. 115-139 (1994).

Gravina, S.A., et al., "Biomimetic In Vitro Assay for the Characterization of Bitter Tastants and Identification of Bitter Taste Blockers," in *Challenges in Taste Chemistry and Biology*, Hofmann, T., et al., eds., Chapter 6, pp. 91-101, Presented at the *224th ACS National Meeting & Exposition* (2002), American Chemical Society (Published 2004).

Harder, D.B., et al., "Assessing gustatory detection capabilities using preference procedures," *Chemical Senses* 14:547-564, IRL Press (1989).

Hayashi, T., et al., "Sensory Study of Flavour Compounds in Extracts of Salted Salmon Eggs (Ikura)," *J. Sci. Food Agric.* 50:343-356, Elsevier Applied Science (1990).

Hwang, D.-F., et al., "Seasonal variations of free amino acids and nucleotide-realted compounds in the muscle of cultured Taiwanese puffer *Takifugu rubripes*," *Fisheries Science* 66:1123-1129, Blackwell Publishing (2000).

Jingami, H., et al., "Structure of the metabotropic glutamate receptor," *Curr. Opin. Neurobiol.* 13:271-278, Elsevier Science (2003).

Koga, K., et al., "Free Amino Acids, Carnosine and 5'-Inosinic Acid Contents in the Beef Loin and Beef Round," *Mem. Fac. Agr. Kagoshima Univ.* 23:121-129, (1987).

Komata, Y., "Umami Taste of Seafoods," *Food Rev. Intl.* 6:457-487, Marcel Dekker, Inc. (1990).

Kuramitsu, R., Quality Assessment of a Low-Salt Soy Sauce Made of a Salty Peptide or Its Related Compounds, *Adv. Exp. Med. Biol.* 542:227-238, KluwerAcademic/Plenum Publishers (2004).

Kuramitsu, R., et al., "Tastes Produced by Peptides Containing Ionic Groups and by Related Compounds," *Biosci. Biotech. Biochem.* 60:1637-1642, Japan Society for Bioscience, Biotechnology, and Agrochemistry (1996).

Lee, K.-H., et al., "Seasonal Variations of Taste Components in Warty Sea Squirt (*Styela clava*)," *J. Korean Soc. Food. Nutr.* 24:274-279, Mary Ann Liebert, Inc. Publishers (1995).

Maehashi, K., et al., "Isolation of Peptides from an Enzymatic Hydrolysate of Food Proteins and Characterization of Their Taste Properties," *Biosci. Biotechnol. Biochem.* 63:555-559, Japan Society for Bioscience, Biotechnology, and Agrochemistry (1999).

McGregor, R., "Taste Modification in the Biotech Era," *FoodTechnology* 58:24-30, Institute of Food Technologists (May 2004).

McGregor, R.A. and Gravina, S.A., "Studies on the blocking of bitter taste," Abstract presented at the *Association of ChemoReceptor Sciences Meeting* (2001).

Michikawa, K. and Konosu, S., "Sensory Identification of Effective Components for Masking Bitterness of Arginine in Synthetic Extract of Scallop," presented at the *Olfaction and Taste XI Proceedings of the 11th International Symposium on Olfaction and Taste and of the 27th Japanese Symposium on Taste and Smell*, Jul. 12-16, 1993, Springer-Verlag, p. 278 (1994).

Ming, D., et al., Blocking taste receptor activation of gustducin inhibits gustatory responses to bitter compounds, *Proc. Natl. Acad. Sci. USA* 96:9903-9908, The National Academy of Sciences (1999).

Mojet, J., et al., "Effect of Concentration on Taste-Taste Interactions in Foods for Elderly and Young Subjects," *Chem. Senses* 29:671-681, Oxford University Press (Oct. 2004).

Nakata, T., et al., "Role of Basic and Acidic Fragments in Delicious Peptides (Lys-Gly-Asp-Glu-Ser-Leu-Ala) and the Taste Behavior of Sodium and Potassium Salts in Acidic Oligopeptides," *Biosci. Biotech. Biochem.* 59:689-693, Japan Society for Bioscience, Biotechnology, and Agrochemistry (1995).

Communication from ConAgra Foods, Inc. to the Food and Drug Administration Regarding Food Labeling; Nutrient Content Claims, Definitions of Sodium Levels For The Term "Healthy" Docket Nos. 91N-304H and 96P-0500, pp. 1-9, mailed Nov. 30, 2004.

Noguchi, M., et al., "On the Bitter-Masking Activity of a Glutamic Acid-Rich Oligopeptide Fraction," *J. Food. Sci.* 40:367-369, Institute of Food Technologists (1975).

Ohyama, S., et al, "Synthesis of Bitter Peptides Composed of Aspartic Acid and Glutamic Acid," *Agric. Biol. Chem.* 52:871-872, The Agricultural Chemical Society of Japan (1988).

"Salt-Free Salt," *Nutrition Rev.* 43:337-338, Nutrition Foundation (1985).

Schiffman, S.S., et al., "Effect of the Nucleoside Analogs Zidovudine, Didanosine, Stavudine, and Lamivudine on the Sense of Taste," *Nutrition* 15:854-859, Elsevier Science Inc. (1999).

Schiffman, S.S., et al., "Modulators of the Adenylate Cyclae System Can Alter Electrophysiological Taste Responses in Gerbil," *Pharm. Biochem. Behavior 48*:983-990, Elsevier Science Inc.(1994).

Seki, T., et al., "Further Study on the Salty Peptide Ornithyl-β-alanine. Some Effects of pH and Additive Ions on the Saltiness," *J. Agric. Food. Chem. 38*:25-29, American Chemical Society (1990).

Shiau, C.-Y., et al., "Extractive Nitrogenous Components of Oysters (*Crassostrea virginica*) and Their Released Liquors," *J. Fish. Soc. Taiwan 21*:281-291, Fisheries Society of Taiwan (1994).

Shirai, T., et al., "Taste Components of Japanese Spiny and Shovel-Nosed Lobsters," *Fisheries Science 62*:283-287, Blackwell Publishing (1996).

Tada, M., et al., "L-Orinthyltaurine, a New Salty Peptide," *J. Agric. Food Chem. 32*:992-996, American Chemical Society (1984).

Tamura, M., et al., "An Enhancing Effect on the Saltiness of Sodium Chloride of Added Amino Acids and Their Esters," *Agric. Biol. Chem. 53*:1625-1633, The Agricultural Chemical Society of Japan (1989).

Tamura, M., et al., "Mechanism for the Bitter Tasting Potency of Peptides Using *O*-Aminoacyl Sugars as Model Compounds," *Agric. Biol. Chem. 54*:1401-1409, Japan Society for Bioscience, Biotechnology, and Agrochemistry (1990).

Tamura, M., et al., "Practical Debittering Using Model Peptides and Related Compounds," *Agric, Biol. Chem. 54*:41-51, Japan Society for Bioscience, Biotechnology, and Agrochemistry (1990).

Tamura, M., et al., "Structural Correlation between Some Amides and a Taste Receptor Model," *J. Agric. Food Chem. 37*:737-740, American Chemical Society (1989).

Tamura, M., et al., "The Relationship between Taste and Primary Structure of "Delicious Peptide" (Lys-Gly-Asp-Glu-Glu-Ser-Leu-Ala) from Beef Soup," *Agric. Biol. Chem. 53*:319-325, The Agricultural Chemical Society of Japan (1989).

*The Merck Index: An Encyclopedia of Chemicals, Drugs, and Biologicals*, 12th Ed., Budavari, S., et al., eds., Merck Research Laboratories, pp. 456, 779-780, 854, and 1553 (1996).

Xu, H., et al., "Different functional roles of T1R subunits in the heteromeric taste receptors," *Proc. Natl. Acad. Sci. Early Edition* pp. 1-6, The National Academy of Sciences, published online at www.pnas.org/cgi/doi/10.1073/pnas.0404384101 (2004).

Yamaguchi, S., "Basic Properties of Umami and Effects on Humans," *Phys. Behavior 49*:833-841, Pergamon Press (1991).

Yamaguchi, S., "The Synergistic Taste Effect of Monosodium Glutamate and Disodium 5'-Inosinate," *J. Food Sci. 32*:473-478, Institute of Food Technologists (1967).

Yang, S.-T. and Lee, E.-H., "Taste Compounds of Fresh-Water Fishes," *Bull. Korean Fish. Soc. 17*:170-176, Pusan: Han'guk Susan Hakhoe (1984).

International Search Report for International Application No. PCT/US99/30610, European Patent Office, mailed Jul. 17, 2000.

Co-pending U.S. Appl. No. 11/155,738, inventors Salemme, F.R., et al., filed Jun. 20, 2005 (not published).

COMPOSITIONS AND METHODS FOR PRODUCING A SALTY TASTE IN FOODS OR BEVERAGES

BACKGROUND OF THE INVENTION

1. Field of the Invention

The invention relates to substitutes for common table salt in food and beverages. More specifically, the present invention relates to compositions containing bitterness inhibitors that reduce the bitter taste, and increase the salty taste, of potassium chloride used in foods or beverages as a substitute for sodium chloride. The compositions contain as bitterness inhibitors mixtures of taurine or a physiologically acceptable salt thereof, with 5'-nucleotide monophosphates or physiologically acceptable salts thereof. Furthermore, the present invention relates to methods of using these compositions and methods for preparing them.

2. Background Art

The sensation of taste has a profound biological significance with ramifications beyond providing people with pleasurable culinary experiences. Taste conveys many cues to humans and other animals. For example, the ability to taste allows us to identify tainted or spoiled foods, and provides satisfying responses that may be proportionate to caloric or nutritive value.

There are generally considered to be five categories of taste: sweet, sour, bitter, salty and umami (savory) (McGregor, R., *Food Technol.* 58(5):24-30 (2004)). These can be sub-classified as the appetitive tastes salty, sweet and umami, and the aversive tastes bitter and sour. The appetitive tastes are pleasurable and are associated with nutrient-containing foods. The aversive tastes may be elicited by toxic compounds, and thereby protect an animal by discouraging the ingestion of unhealthy or dangerous foods. Each of these tastes results from substances that may be referred to as "tastants."

A well known salty tastant is sodium chloride (i.e., common table salt, NaCl). Sodium chloride is found in many different types of foods, condiments and beverages. Sodium chloride is also added to foods, condiments and beverages to make them more enjoyable. Unfortunately, excessive intake of sodium can increase the risk of high blood pressure and heart disease. Despite recommendations from the National Institutes of Health that persons should consume no more than 2400 mg of sodium per day, surveys show that Americans greatly exceed this amount. In fact, Americans consume more than double the recommended amount per day. This fact has prompted efforts to develop salt substitutes that contain a reduced amount of sodium.

One approach is to substitute potassium chloride as a saltening agent either partially, or wholly, for sodium chloride (Kuramitsu, R. *Advances in Exp. Med. Biol.*, 542:227-238 (2004)). There are potassium chloride products on the market, such as Cardia Salt®, No Salt®, Morton Salt Substitute® (U.S. Pat. No. 3,505,082), and AlsoSalt® (U.S. Pat. No. 5,897,908). Many of these products include agents, such as L-lysine, to modify or mask the unpleasant taste of potassium chloride.

Recent nutritional guidelines not only suggest that the amount of sodium in the diet (ingested principally as sodium chloride) should be reduced, but that the amount of potassium in the diet should be increased. (Colorado State University Cooperative Extension-Nutrition Resources: Fact Sheet No. 9.355 "*Potassium and Health*" by J. Anderson, et al. (accessed May 15, 2005)). Potassium is involved in nerve function, muscle control and blood pressure. An insufficient potassium level in the body may, for example, cause muscle cramping during exercise, or cardiovascular irregularities. Id.

Consequently, substituting dietary potassium chloride for sodium chloride could provide at least two health benefits. First, it would reduce sodium intake, which could decrease risk of hypertension and associated heart disease. Second, it would increase potassium intake, which is below recommended levels in most modern diets. Despite these benefits, substituting potassium chloride for sodium chloride faces a major obstacle because potassium has a strong bitter taste.

Another obstacle to the development of a palatable potassium chloride salt substitute is the requirement that flavorings added to food or beverages meet Flavor and Extract Manufacturers Association, Generally Recognized as Safe (FEMA GRAS) guidelines or be approved by the U.S. Food and Drug Administration. Substances that might be used to inhibit the bitter taste of potassium must meet these guidelines. The use of bitterness inhibitors not already accepted by FEMA GRAS present increased development costs and delayed market entry for food and beverage companies trying to develop better salt substitutes.

Attempts to eliminate the bitter taste of potassium chloride have taken two distinct approaches. One is to use "maskers" to cover the bitter taste. These maskers are highly flavorful ingredients such as onion, garlic, paprika, red pepper, chili powder, and other spices. None of these mixtures have found wide-spread acceptance, probably because the bitter taste of potassium is still detectable. The second approach is to use compounds that reduce the bitter taste of potassium without imparting another unpleasant taste. U.S. Pat. No. 5,631,299, Kurtz et al., discloses that taurine may reduce the bitter taste of potassium chloride without producing another unpleasant taste, if used in the right amount. (See U.S. Pat. No. 5,631, 299, which is incorporated by reference in its entirety).

Methods for identifying compounds that reduce bitter taste (e.g., the inhibition of activation of taste receptors) have been described by Margolskee et al. in U.S. Pat. No. 6,540,978, which is incorporated by reference in its entirety. Such methods have resulted in the identification of compounds such as 5'-adenosinic acid (AMP) and 5'-inosinic acid (IMP) as potential "bitterness inhibitors."

Other examples of compounds proposed for use in a salt substitute to reduce or mask the bitter taste of potassium chloride include fumaric acid (U.S. Pat. No. 3,505,082), lactose and/or dextrose and cream of tartar (U.S. Pat. No. 3,860, 732), potassium phosphate (U.S. Pat. No. 4,243,691) autolyzed yeast (U.S. Pat. No. 4,297,375), lysine monohydrochloride (U.S. Pat. No. 5,897,908), and specific combinations of sulfate-containing and chloride containing salts (U.S. Pat. No. 6,541,050).

Existing approaches for blocking the bitterness of potassium in salt substitutes have been unsuccessful because they do not reduce bitterness to a level satisfactory to consumers. Therefore, the undesirable bitter taste of potassium chloride remains a problem. In fact, some major food and beverage companies have objected to regulations that would lower the maximum amount of sodium allowed in foods labeled healthy, because consumers would not find these foods palatable, and viable substitutes for sodium chloride are unavailable. (See comments by ConAgra Foods to the FDA on Nov. 30, 2004 and by Quaker Foods & Beverages to the FDA on Jul. 10, 2003 regarding the FDA proposed regulations for a more restrictive sodium level).

BRIEF SUMMARY OF THE INVENTION

The present invention provides compositions for producing a salty taste in foods or beverages. These compositions contain potassium chloride (KCl), and bitterness inhibitors. These inhibitors comprise mixtures of taurine or a physiologically acceptable salt thereof, with a 5'-nucleotide monophosphate comprising 5'-adenosinic acid (AMP), 5'-inosinic acid (IMP), combinations of AMP and IMP, combinations of AMP, IMP and 5'-guanylic acid (GMP) or physiologically acceptable salts thereof. The invention also includes methods of using the bitterness inhibitors to decrease the bitter taste and increase the salty taste of potassium chloride in foods or beverages, and to methods of manufacturing these compositions.

By providing an enjoyable substitute for sodium chloride, the invention allows individuals to decrease sodium intake and increase potassium intake, leading to a healthier diet.

The present invention overcomes the disadvantages of existing salt substitutes, because the compositions of the invention have a superior ability to reduce the bitterness of KCl. In particular, the taurine/5'-nucleotide monophosphate combinations mentioned above produce a greater effect on the reduction of the bitterness of KCl, than does the administration of taurine alone or the administration of any of these 5'-nucleotide monophosphates alone. The present invention can also increase the salty taste of KCl containing foods or beverages, and enhance savory flavors in these foods or beverages.

Another benefit of the invention is that it provides a composition for reducing the bitter taste and increasing the salty taste of a KCl salt substitute that is cheaper than compositions relying only on AMP to reduce bitterness. Particularly, the present invention requires less AMP than compositions in which AMP is the only bitterness inhibitor, because the present invention supplements or replaces AMP with taurine and other 5'-nucleotide monophosphates. Because AMP is significantly more expensive than taurine and than other 5'-nucleotide monophosphates such as IMP and GMP, the present invention provides a salt substitute that is not only palatable but economical.

Moreover, KCl, taurine, AMP, IMP and GMP are already accepted as meeting Flavor and Extract Manufacturers Association, Generally Recognized as Safe (FEMA GRAS) guidelines.

The present invention provides a composition comprising a food or beverage comprising (a) potassium chloride in an amount effective to induce a bitter taste and induce a salty taste, (b) taurine or a physiologically acceptable salt thereof, and (c) a 5'-nucleotide monophosphate, comprising 5'-adenosinic acid (AMP) or 5'-inosinic acid (IMP) or a physiologically acceptable salt thereof, wherein the taurine and the 5'-nucleotide monophosphate are present in an amount effective to reduce the bitter taste of the potassium chloride, and wherein the composition is not seafood and is not an extract of seafood. The 5'-nucleotide monophosphate may also be combinations of AMP and IMP, combinations of AMP, IMP and GMP or physiologically acceptable salts thereof.

The present invention also provides a salt substitute consisting essentially of (a) potassium chloride, wherein the potassium chloride is present in an amount effective to induce a bitter taste and induce a salty taste, (b) taurine or a physiologically acceptable salt thereof, and (c) a 5'-nucleotide monophosphate comprising AMP or IMP or a physiologically acceptable salt thereof, wherein the taurine and 5'-nucleotide monophosphate are present in an amount effective to reduce the bitter taste of the potassium chloride. The 5'-nucleotide monophosphate may also be combinations of AMP and IMP, combinations of AMP, IMP and GMP or physiologically acceptable salts thereof.

In addition, the invention provides a composition comprising tastands consisting essentially of (a) taurine or a physiologically acceptable salt thereof, and (b) a 5'-nucleotide monophosphate selected from the group consisting of AMP, IMP, combinations of AMP and IMP, combinations of AMP, IMP and GMP, or physiologically acceptable salts thereof, wherein the tastands are present in an amount effective to reduce a bitter taste of potassium chloride.

The invention also provides a method of reducing sodium intake and increasing potassium intake in the diet of an individual, comprising administering to the individual the compositions or salt substitute of the invention.

Another aspect of the invention is a method for preparing the compositions of the invention comprising adding to the food or beverage (a) an amount of potassium chloride effective to induce a bitter taste and induce a salty taste, (b) an amount of taurine or a physiologically acceptable salt thereof, and (c) an amount of a 5'-nucleotide monophosphate wherein the 5'-nucleotide monophosphate comprises AMP or IMP or a physiologically acceptable salt thereof, and wherein the amount of taurine and the amount of 5'-nucleotide monophosphate are effective to reduce the bitter taste of the potassium chloride.

DETAILED DESCRIPTION OF THE INVENTION

The present invention provides compositions, for use in foods or beverages, the compositions containing taurine or a physiologically acceptable salt thereof, and a 5'-nucleotide monophosphate selected from the group consisting of AMP, IMP, combinations of AMP and IMP and physiologically acceptable salts thereof. The combinations may also contain GMP or a physiologically acceptable salt thereof. These compositions are added to KCl table salt substitutes, or to foods or beverages containing KCl as a table salt substitute. The invention also includes methods for reducing the bitter taste of KCl to a satisfactory level, and methods of manufacturing the compositions of the invention.

The specification uses a number of terms from the food taste industry. To provide a clear and consistent understanding of the specification and claims, including the scope to be given such terms, the following definitions are provided.

The term "salt substitute" as used herein is a composition of KCl, taurine or a physiologically acceptable salt thereof, and a 5'-nucleotide monophosphate selected from the group consisting of AMP or IMP and/or GMP, mixtures thereof and physiologically acceptable salt thereof.

The term "taurine" as used herein is 2-aminoethanesulfonic acid or a physiologically acceptable salt thereof. This salt can be a sodium or non-sodium salt. In the case of sodium salt, the amount of sodium added to the compositions of the present invention by such salt is negligible relative to the overall mixture.

The term "5-nucleotide monophosphate" as used herein is 5'-inosinic acid (IMP), 5'-guanylic acid (GMP), and 5'-adenylic acid (AMP), physiologically acceptable salt(s) thereof, or mixtures of the acid(s) and/or salt(s). These salts can be sodium or non-sodium salts. In the case of sodium salts, the amount of sodium added to the compositions of the present invention by such salts is negligible relative to the overall mixture.

The term "food" as used herein is a composition to which sodium chloride may be added to enhance the flavor. Such foods include, but are not limited to, soup, broth, gravy, soy sauce, meats (including raw, cooked, and dried meats), vegetables (including raw, pickled, cooked, and dried vegetables, such as french fries), fruits (including raw, cooked, and dried fruits), grains (including dried cereals and breads), prepared foods (including dried, canned, or jarred sauces and soups), snack foods (such as Fritos® Chili Cheese flavored corn chips, potato chips, cheese puffs, pretzels, nuts and crackers), various types of noodles (such as macaroni and spaghetti), salt-preserved food, and various types of cheese, butter, margarine, and condiments such as ketchup, mustard and steak sauce.

The term "beverage" as used herein is a composition in a single strength, ready-to-serve drinkable form, or a concentrate that can be diluted with water to form a drinkable composition. Examples of beverages of the present invention typically comprise sports drinks, tomato juice, cola, and water with salt added, pickle juice.

The term "seafood" as used herein includes edible fish (including all fresh or saltwater fish), shellfish (including abalone, crab, mussel, crawfish, clam, lobster, oyster, shrimp, squid, scallops, etc.), crustaceans, roe and any other form of edible aquatic animal life.

The term "tastant" as used herein is a compound or molecular complex that induces, in a subject, the perception of taste. For example, a "bitter tastant" as used herein is defined as a compound or molecular complex that induces, in a subject, the perception of a bitter taste. Examples of bitter tastants include, but are not limited to, KCl, denatonium benzoate, quinine hydrochloride, strychnine hydrochloride, nicotine hemisulfate, atropine hydrochloride, sparteine, naringin, caffeic acid (caffeine), quinacrine, and epicatechin (See Ming et al., 1999, Proc. Natl. Acad. Sci. U.S.A. 96:9903-9908, incorporated by reference herein).

The term "tastand" as used herein is a compound that, when ingested at an appropriate concentration along with a tastant having an undesirable taste, will eliminate or substantially reduce the undesirable taste without inducing a taste of its own at its usage level. Examples of tastands that decrease or abrogate the perception of bitterness of bitter tastants are specifically termed "bitterness inhibitors." Examples of such bitterness inhibitors include, but are not limited to, taurine, AMP, IMP and GMP.

The term "umami" as used herein is defined as that flavor which is perceived as savory, such as is associated with meats, chicken broth and seasonings containing monosodium glutamate.

The term "amount effective" as used herein is the amount that subjectively, and significantly, affects the perception of taste as evaluated by the sensory analysis experiments described in the Examples below. The desired effects include, but are not limited to, a decrease in the perception of bitter taste, an increase in the perception of salty taste and an increase in the perception of umami taste or savory taste. The effectiveness of a composition is determined, e.g., by comparing scores given by a panel of taste testers for taste attributes such as bitterness, saltiness, and umami flavor, between two samples (e.g., reduced sodium chicken broth+KCl+taurine+AMP vs. reduced sodium chicken broth+KCl).

The term "individual" as used herein is defined as a human or other mammal such as a cat or dog.

The term "administer" as used herein is defined as the ingestion of a composition of the present invention by an individual, alone or with the assistance of another.

The present invention includes a salt substitute or a food composition containing the salt substitute. The salt substitute may be used as a table top seasoning or an ingredient in a food or beverage. The composition may comprise taurine or a physiologically acceptable salt thereof, a 5'-nucleotide monophosphate or a physiologically acceptable salt thereof, and KCl, or the composition may consist of essentially taurine or a physiologically acceptable salt thereof, and a 5'-nucleotide monophosphate or a physiologically acceptable salt thereof, for use in KCl containing compositions. Furthermore, the composition may contain flow agents, processing agents, sugars, amino acids, other nucleotides, or sodium or potassium salts of organic acids such as citrate and tartarate, to add flavor, or to aid blending, processing or flow properties of the composition.

The present invention may be used to improve the taste of salt substitutes, foods or beverages containing KCl by decreasing or eliminating the bitter taste of KCl, increasing the salty taste of KCl, and increasing an umami flavor in the food or beverage.

If a bitter tastant is a preservative, the bitterness inhibitors of the invention may permit or facilitate its incorporation into foods or beverages, thereby improving food or beverage safety. For foods or beverages administered as nutritional supplements, the incorporation of inhibitors of the invention may encourage ingestion, thereby enhancing the effectiveness of these compositions in providing nutrition or calories to a subject.

Any acceptable method for preparing the present compositions can be used. A composition of the present invention may be prepared by combining the ingredients below, KCl, taurine and 5'-nucleotide monophosphate. The ingredients may be mixed together before they are added to the food or beverage, or they each may be added separately to the food or beverage. The ingredients may be added in powder or liquid form.

The mixing ratio for the salt substitute can be adapted according to the purpose of use of the salt substitute. For example, the salt substitute may be used on its own or may include common table salt (NaCl) in any ratio depending on the specific application and desired level of NaCl reduction in the final product. Similarly, the tastands of the present invention will be added in amounts dependent on the amount of bitter tastant in the composition.

Typically, the salt substitute of the present invention will be added to the food or beverage to provide an amount of KCl that is approximately the same weight amount as the NaCl that is being replaced. For example, the amount of KCl in the food or beverage after the salt substitute is added may range from about 0.5 to about 1.5 times the replaced NaCl depending upon the application, i.e., if about 0.5 mg of NaCl is removed, about 0.25 to about 0.75 mg of KCl is added. The amounts of NaCl conventionally used to season various food or beverage products are well known to those of skill in the art and need not be recited.

The amount of KCl added to a composition will vary depending on the amount of perceived saltiness desired and other compounds present in the composition. For example, KCl may be present at a concentration between about 0.5% and about 1.5%, preferably about 0.9% (about 9000 ppm), of the food or beverage.

One ingredient employed in the present invention is taurine or a physiologically acceptable salt thereof. The amount of taurine or a physiologically acceptable salt thereof added to a composition comprising a bitter tastant will vary depending on the amount of bitter tastant present and other compounds present in the composition. For example, taurine may be present at a concentration between about 1% and about 15% w/w KCl. Preferably, the food or beverage composition comprises between about 400 and about 1200 ppm of taurine, more preferably about 750 ppm of taurine.

An additional ingredient of the present invention is a 5'-nucleotide monophosphate, AMP, IMP, GMP, combinations thereof, or physiologically acceptable salts thereof. The amount of 5'-nucleotide monophosphate or a physiologically acceptable salt thereof added to a composition comprising a bitter tastant will vary depending on the amount of bitter tastant present and other compounds present in the composition. For example, the 5'-nucleotide monophosphate AMP may be present at a concentration between about 1% and about 9% w/w KCl. Preferably, the concentration in a food or beverage is between about 100 and about 800 ppm of AMP, more preferably about 600 ppm of AMP. The 5'-nucleotide monophosphates IMP and/or GMP may be present at a concentration up to about 8% w/w KCl. Preferably, the concentration in a food or beverage is up to about 600 ppm of IMP, more preferably between about 100 and about 200 ppm of IMP, and/or up to about 600 ppm of GMP, more preferably between about 100 and about 200 ppm of GMP.

A preferred embodiment of the claimed invention is a salt substitute comprised of between about 80% and about 98% KCl, between about 2% and about 15% taurine or a physiologically acceptable salt thereof, between about 1% and about 8% AMP or a physiologically acceptable salt thereof, up to about 4% IMP or a physiologically acceptable salt thereof, and up to about 4% GMP or a physiologically acceptable salt thereof. These percentages are based on the amounts of these ingredients relative to the total weight of all of these ingredients.

In another preferred embodiment of the claimed invention, the salt substitute is comprised of between about 83% and about 87% KCl, between about 6% and about 8% taurine or a physiologically acceptable salt thereof, between about 3% and about 6% AMP or a physiologically acceptable salt thereof, or between about 1% and about 3% IMP or a physiologically acceptable salt thereof. These percentages are based on the amounts of these ingredients relative to the total weight of all of these ingredients.

In another preferred embodiment of the claimed invention, the salt substitute is comprised of between about 83% and about 87% KCl, between about 6% and about 8% taurine or a physiologically acceptable salt thereof, between about 3% and about 6% AMP or a physiologically acceptable salt thereof, up to about 3% IMP or a physiologically acceptable salt thereof, and up to about 3% GMP or a physiologically acceptable salt thereof. These percentages are based on the amounts of these ingredients relative to the total weight of all of these ingredients.

In a more preferred embodiment of the claimed invention, the salt substitute is comprised of about 86.95% KCl, about 3.86% AMP (monosodium salt of adenosinic acid), about 7.25% taurine, about 0.97% IMP (disodium salt of inosinic acid) and about 0.97% GMP (disodium salt of guanylic acid). These percentages are based on the amounts of these ingredients relative to the total weight of all of these ingredients.

In another preferred embodiment of the claimed invention, the composition comprises tastands consisting essentially of between about 40% and about 80% taurine or a physiologically acceptable salt thereof, and between about 20% and about 60% 5'-nucleotide monophosphate or a physiologically acceptable salt thereof. These percentages are based on the amounts of these ingredients relative to the total weight of all of these ingredients.

In a more preferred embodiment of the claimed invention, the composition comprises tastands consisting essentially of about 55% taurine or a physiologically acceptable salt thereof, about 30% AMP or a physiologically acceptable salt thereof, about 7.5% IMP or a physiologically acceptable salt thereof, and about 7.5% GMP or a physiologically acceptable salt thereof. These percentages are based on the amounts of these ingredients relative to the total weight of all of these ingredients.

In another preferred embodiment of the claimed invention, up to between about 5% and about 10% of the composition comprises flow agents, processing agents, sugars, amino acids, other nucleotides, or sodium or potassium salts of organic acids such as citrate and tartarate.

The salt substitute compositions of the present invention may exist alone as a solid, (e.g., powder or granulate), as a liquid form, or as an ingredient in a food or beverage.

The compositions of the invention comprise a mixture of ingredients in a range of proportions. In liquid foods like soup and gravies, the solids are added in the correct amounts and proportions to the liquid soup, gravy or other prepared foods. In table top applications where the formulation is used dry, the ingredients are mixed into a liquid in the correct proportions, together with non-caking or other agents commonly used in the food industry and known to those practicing the art of food formulation, and then dried and ground. Alternatively, the liquid mixture can be spray dried to form a powered solid suitable for tabletop applications and packaging as a solid salt replacement.

The present composition of the invention may be packaged as a composition of taurine or a physiologically acceptable salt thereof, and a 5'-nucleotide monophosphate or a physiologically acceptable salt thereof. This composition may be added to foods or beverages comprising KCl or KCl and NaCl or may be combined or packaged with NaCl and subsequently added to foods or beverages comprising KCl. Also, the present composition of the invention may be packaged as taurine or a physiologically acceptable salt thereof, a 5'-nucleotide monophosphate or a physiologically acceptable salt thereof, and KCl, or taurine or a physiologically acceptable salt thereof, a 5'-nucleotide monophosphate or a physiologically acceptable salt thereof, KCl and NaCl. These compositions may be added to foods or beverages that comprise KCl, NaCl, both or neither. The composition may be packaged in bulk, in which the package contains more of the composition than would typically be used for a single dish or serving of food or beverage. Such bulk packages can be in the form of paper, plastic, or cloth bags or cardboard boxes or drums. Such bulk packages may be fitted with plastic or metal spouts to facilitate the dispensing of the composition.

Alternatively, the present compositions of the invention may be packaged in an amount that would be suitable for use at a single meal or with a single serving of food or beverage. Suitable packaging materials for such individual serving packages include paper or foil packets or pouches.

EXAMPLES

The following Examples are illustrative, but not limiting, of the compositions and methods of the present invention. Modifications of these examples according to conditions and parameters normally encountered in taste biology and chemistry that are obvious to those skilled in the art, in view of the present disclosure, are within the spirit and scope of the invention.

9

Example 1

Materials and Methods for Sensory Analysis

ABIC International Consultants, a sensory evaluation contract research group in Fairfield, N.J., convened an expert taste panel of 18 individuals selected for their taste acuity, particularly with regard to bitterness level. This panel evaluated a number of chicken broth samples containing various ingredients.

Methods for qualifying and quantifying the different types of tastes of sample compositions have been described in publications. Such methods are often referred to as sensory testing or sensory analysis. Typically, a panel of experienced taste testers evaluate sample compositions and assign a numeric value to each composition, based on their perceptions of the type and intensity of the tastes.

Reduced sodium chicken broth (50% Reduced Sodium, College Inn®) was obtained from a local supermarket. Taurine was obtained as a commercial food ingredient from Ajinomoto (it may also be obtained from Gallard-Schlesinger). AMP (monosodium salt thereof) was obtained as a commercial food ingredient from Xinxiang Tuoxin Biochemical Technology & Science Co., Ltd. IMP and GMP (disodium salts thereof) were obtained from Ajinomoto as a 50/50 mixture called Ribotide®. KCl and NaCl were obtained from Morton Salt Co. as commercial food ingredients. Ingredients were added as dry powders to the canned soup product College Inn® Reduced Sodium Chicken Broth (obtained from the supermarket) in the correct amounts and proportions to achieve the desired final concentrations in the broth specified (as a % w/w or ppm) in Table 1.

College Inn® Reduced Salt Chicken Broth contains approximately 50% of the NaCl that is typically present in fully salted chicken broth products. All chicken broth samples were fortified with 0.9% KCl. Various combinations of taurine (750 ppm), AMP (600 ppm) and IMP (200 ppm) were added to the fortified chicken broth as described in Table 1.

Samples were prepared in a preparation lab at ABIC and were presented to the judges labeled only with triple digit random number codes. The soup was served to the judges at 160° F. Samples were presented to the judges sequentially with a rest period of at least 15 minutes between samples. To eliminate bias, the order of sample presentation was randomized. Judges were provided with unsalted crackers and water between samples.

The taste panel evaluated the intensity of the samples for the attributes of perceived saltiness, chicken (umami) flavor, and bitterness. The evaluation range for the attributes was 0 (none) to 8 (very salty), 0 (none) to 8 (very strong), and 0 (none) to 8 (very bitter), respectively. Scores from all 18 taste testers for each attribute were averaged for each sample. These average scores are presented in Table 1.

Results 0.9% KCl+AMP (600 ppm)+taurine (750 ppm)    (Sample 3)

As shown in Table 1, the bitterness score for Sample 3 (KCl+AMP+taurine) was 1.22. The bitterness score of the Control was 3.47. Therefore, the combination of AMP and taurine added to KCl in Sample 3 produced a significant reduction in bitterness as compared to the Control. In addition, Sample 3 produced a lower bitterness score compared to AMP alone in Sample 1 (1.72, KCl+AMP), and taurine alone in Sample 2 (2.06, KCl+taurine).

Sample 3 produced a saltiness score of 3.39. This was greater than the saltiness score of the Control (2.89). The saltiness score of Sample 3 (KCl+taurine+AMP) was unexpected, because the score of Sample 1 (KCl+AMP) was 3.19, which was higher than the Control, but the score of Sample 2 (KCl+taurine) was 2.42, which was lower than the Control. Thus, while AMP increases perception of saltiness, taurine suppresses it. Accordingly, a combination of AMP and taurine would have been expected to produce a perceived saltiness score between 3.19 and 2.42, approximately (i.e. between the score for KCl+AMP and the score for KCl+taurine). However, Sample 3 had a score of 3.39, which represents an unexpectedly substantial increase in salty taste.

Moreover, Sample 3 produced an umami (chicken) flavor score of 3.91, a significant increase over the Control score of 3.13 for the same attribute.

0.9% KCl+IMP (200 ppm)+taurine (750 ppm)    (Sample 5)

The bitterness score for Sample 5 (KCl+IMP+taurine) was significantly lower than the bitterness score for the Control (1.72 vs. 3.47). Also, compared to Sample 2 (KCl+taurine) and Sample 4 (KCl+IMP), which had scores for bitterness of 2.06 and 3.25, respectively, the combination of IMP and taurine in Sample 5 produced a significantly greater effect on the reduction of bitterness.

Sample 5 produced a saltiness score of 2.72, less than the saltiness score for the Control (2.89). The saltiness score of Sample 5 was unexpectedly high in view of the scores for samples 2 and 4. The saltiness scores of Sample 2 (KCl+taurine) and Sample 4 (KCl+IMP) were both lower than the Control (2.42 and 2.61, respectively). Sample 5 (KCl+taurine+IMP) would therefore not have been expected to have a score higher than either Sample 2 or Sample 4.

Example 2

Materials and Methods for Sensory Analysis

Samples of chicken broth with different dosing combinations of taurine, AMP, IMP and GMP were given to a panel of 18 experienced taste testers by ABIC. The materials and

TABLE 1

Summary of Taste Variable Scores of 50% Reduced Sodium College Inn ® Chicken Broth

| Sample No. | Groups | NaCl (ppm) | KCl (ppm) | AMP (ppm) | Taurine (ppm) | IMP (ppm) | Count | Salt (0-8) | Chicken (umami) (0-8) | Bitter (0-8) |
|---|---|---|---|---|---|---|---|---|---|---|
| Control | KCl | 18750 | 9000 | 0 | 0 | 0 | 18 | 2.89 | 3.13 | 3.47 |
| 1 | KCl + AMP | 18750 | 9000 | 600 | 0 | 0 | 18 | 3.19 | 4.06 | 1.72 |
| 2 | KCl + taurine | 18750 | 9000 | 0 | 750 | 0 | 18 | 2.42 | 2.97 | 2.06 |
| 3 | KCl + AMP + taurine | 18750 | 9000 | 600 | 750 | 0 | 18 | 3.39 | 3.91 | 1.22 |
| 4 | KCl + IMP | 18750 | 9000 | 0 | 0 | 200 | 18 | 2.61 | 3.38 | 3.25 |
| 5 | KCl + IMP + taurine | 18750 | 9000 | 0 | 750 | 200 | 18 | 2.72 | 3.22 | 1.72 | methods used in this test were the same as those in Example 1. However, an additional Control containing full sodium (NaCl, Control 1), and more variations of concentrations of taurine, AMP, IMP and GMP were tested. The compositions of the broth samples and average scores for each are presented in Table 2.

TABLE 2

Dosing Studies

| Sample No. | Groups | NaCl (ppm) | KCl (ppm) | AMP (ppm) | Taurine (ppm) | IMP (ppm) | GMP (ppm) | Count | Salt (0-8) | Chicken (0-8) | Bitter (0-8) |
|---|---|---|---|---|---|---|---|---|---|---|---|
| Control 1 | Full Salt (NaCl) | 38750 | 0 | 0 | 0 | 0 | 0 | 18 | 4.11 | 3.56 | 0.44 |
| Control 2 | KCl | 18750 | 9000 | 0 | 0 | 0 | 0 | 18 | 2.11 | 1.89 | 2.83 |
| 1 | KCl + taurine + AMP + IMP | 18750 | 9000 | 400 | 750 | 200 | 0 | 18 | 2.22 | 2.19 | 2.06 |
| 2 | KCl + taurine + AMP + IMP + GMP | 18750 | 9000 | 400 | 750 | 100 | 100 | 18 | 2.42 | 2.33 | 1.64 |
| 3 | KCl + taurine + AMP + IMP + GMP | 18750 | 9000 | 200 | 750 | 200 | 200 | 18 | 2.25 | 2.50 | 1.92 |
| 4 | KCl + taurine + AMP | 18750 | 9000 | 600 | 750 | 0 | 0 | 18 | 2.22 | 2.47 | 1.61 |
| 5 | KCl + taurine + AMP | 18750 | 9000 | 600 | 400 | 0 | 0 | 18 | 2.64 | 2.64 | 2.00 |
| 6 | KCl + taurine + AMP | 18750 | 9000 | 600 | 1200 | 0 | 0 | 18 | 2.58 | 3.03 | 1.86 |

Results 0.9% KCl+AMP (600 ppm)+taurine (750 ppm)      (Sample 4)

As shown in Table 2, the bitterness score for Sample 4 (1.61, KCl+taurine+AMP) was significantly lower than the score for Control 2 (2.83, Reduced Sodium chicken broth with KCl). This indicates that the combination of taurine and AMP added to KCl is highly effective in lowering bitterness. Use of lower and higher amounts of taurine (Samples 5 and 6, 400 ppm and 1200 ppm, respectively) with the same amount of KCl and AMP as in Sample 4 also produced lower bitterness scores compared to Control 2.

0.9% KCl+taurine (750 ppm)+AMP (400 ppm)+
  GMP (100 ppm)+IMP (100 ppm)      (Sample 2)

The bitterness score for Sample 2 (KCl+taurine+AMP+IMP+GMP) was much lower than the bitterness score for Control 2 (1.64 vs. 2.83). This difference in bitterness score was similar to the reduction observed for Sample 4 (1.61 vs. 2.83 for Control 2), suggesting that similar reductions in bitterness can be achieved by substituting a combination of IMP and GMP for a relatively equal amount of AMP.

Example 3

Materials and Methods for Sensory Analysis

A simple beef gravy that is used in the industry and food service was prepared at ABIC according to the following procedure: 3.5% modified starch (Col Flo 67; National Starch) was dispersed in a portion of cold formula water; 2.5% beef base (20-821; Eastern Foods) and 1.2% salt (Morton® Salt) were added to the water and heated to 180° F.; and the starch suspension was added and mixed with the beef base/salt water, which was continually heated until the mixture thickened. Taurine, AMP, IMP and GMP obtained as described in Example 1 were added in various combinations as described in Table 3. KCl was obtained from the Morton Salt Co as a commercial food ingredient. It was added at a concentration of 0.9% w/w of the beef gravy for Samples 2-6. These ingredients were added as dry powders to the beef gravy composition in the correct amounts and proportions to achieve the desired final concentrations.

ABIC assembled an expert panel of 18 testers selected for their taste acuity, particularly with regard to bitterness level.

Samples were prepared in a preparation lab at ABIC and were presented to the judges labeled only with triple digit random number codes. The gravy was served to the judges at 160° F. Samples were presented to the judges sequentially with a rest period of at least 15 minutes between samples. To eliminate bias, the order of sample presentation was randomized. Judges were provided with unsalted crackers and water between samples.

The taste panel evaluated the intensity of the beef gravy samples for the attributes of sweetness, sourness, perceived saltiness, bitterness, beef flavor, and overall flavor. The evaluation range was 0 (none) to 8 (very sweet), 0 (none) to 8 (very sour), 0 (none) to 8 (very salty), 0 (none) to 8 (very bitter), 0 (none) to 8 (very strong), and 0 (none) to 8 (very strong), respectively. The average scores for each attribute are presented in Table 3.

TABLE 3

Summary of Taste Variable Scores of Beef Gravy Test

| Sample No. | Groups | NaCl (%) | KCl (%) | AMP (ppm) | Taurine (ppm) | IMP (ppm) | GMP (ppm) | Count | Sweet (0-8) | Sour (0-8) | Salty (0-8) | Bitter (0-8) | Beef Flavor (0-8) | Overall Flavor (0-8) |
|---|---|---|---|---|---|---|---|---|---|---|---|---|---|---|
| Control 1 | Full Salt (NaCl) | 1.2 | 0 | 0 | 0 | 0 | 0 | 18 | 0.75 | 0.97 | 3.75 | 1.17 | 3.47 | 4.03 |
| Control 2 | 50% Reduced Sodium | 0.6 | 0 | 0 | 0 | 0 | 0 | 18 | 0.19 | 0.31 | 0.72 | 0.69 | 0.94 | 1.06 |
| Control 3 | 50% Reduced Sodium with KCl | 0.6 | 0.9 | 0 | 0 | 0 | 0 | 18 | 0.47 | 0.69 | 2.75 | 2.39 | 2.86 | 3.06 |

TABLE 3-continued

Summary of Taste Variable Scores of Beef Gravy Test

| Sample No. | Groups | NaCl (%) | KCl (%) | AMP (ppm) | Taurine (ppm) | IMP (ppm) | GMP (ppm) | Count | Sweet (0-8) | Sour (0-8) | Salty (0-8) | Bitter (0-8) | Beef Flavor (0-8) | Overall Flavor (0-8) |
|---|---|---|---|---|---|---|---|---|---|---|---|---|---|---|
| 4 | 50% Reduced Sodium with KCl + AMP | 0.6 | 0.9 | 600 | 0 | 0 | 0 | 18 | 0.64 | 1.08 | 3.42 | 1.64 | 3.75 | 4.25 |
| 5 | 50% Reduced Sodium with KCl + AMP + Taurine | 0.6 | 0.9 | 600 | 750 | 0 | 0 | 18 | 0.64 | 1.00 | 3.61 | 2.19 | 3.33 | 3.89 |
| 6 | 50% Reduced Sodium with KCl + AMP + Taurine + IMP + GMP | 0.6 | 0.9 | 400 | 750 | 200 | 200 | 18 | 0.72 | 0.89 | 3.56 | 1.50 | 3.94 | 4.44 |

Results 0.9% KCl+AMP (600 ppm)   (Sample 4)

The saltiness score for Sample 4 (50% reduced sodium with KCl+AMP) was appreciably higher than the saltiness score for Control 3 (3.42 vs. 2.75). In addition, the bitterness score for Sample 4 was 1.64, a substantial reduction compared to the bitterness score for Control 3 (2.39). Thus, addition of AMP resulted in favorable saltiness and bitterness scores for Sample 4 compared to Control 3.

The beef flavor and overall flavor scores for Sample 4 were 3.75 and 4.25, respectively. These scores are a marked increase over the beef flavor and overall flavor scores for all control groups. The beef flavor and overall flavor scores for Sample 4 were greater than the corresponding scores for Control 1 (3.47 and 4.03, respectively). Control 1 was beef gravy containing full sodium.

0.9% KCl+AMP (600 ppm)+taurine (750 ppm)   (Sample 5)

The saltiness score for Sample 5 (50% reduced sodium with KCl+AMP+taurine) was significantly higher than the score for Control 3 (3.61 vs. 2.75). Also, the bitterness, beef flavor, and overall flavor scores for Sample 5 were 2.19, 3.33 and 3.89, respectively. Compared to the corresponding scores for Control 3 (2.39, 2.86 and 3.06, respectively), Sample 5 showed a significant decrease in bitterness and increase in beef flavor and overall flavor. In addition, the scores for sweet and sour tastes were comparable to the scores for Control 1 (full sodium).

0.9% KCl+AMP (400 ppm)+taurine (750 ppm)+
   IMP (200 ppm)+GMP (200 ppm)   (Sample 6)

As shown in Table 3, the bitterness score for Sample 6 (50% reduced sodium, KCl+AMP+taurine+IMP+GMP) was significantly lower than the score for Control 3 (1.50 vs. 2.39). Importantly, in addition to reducing the bitterness, Sample 6 produced a substantially higher saltiness score compared to Control 3 (3.56 vs. 2.75).

The beef flavor score and overall flavor score for Sample 6 were 3.94 and 4.44, respectively. These scores were considerably higher than the beef flavor and overall flavor scores for Control 3 (2.86 and 3.06, respectively). The beef and overall flavor scores for Sample 6 were also greater than the beef and overall flavor scores for Control 1 (3.47 and 4.03, respectively). This is most notable because Control 1 is beef gravy containing full sodium.

In addition, the scores for sweet and sour tastes for Sample 6 were comparable to the scores for Control 1 (full sodium).

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

The invention claimed is:

1. A composition comprising a food or beverage comprising (a) potassium chloride in an amount effective to induce a bitter taste and induce a salty taste, (b) taurine or a physiologically acceptable salt thereof, and (c) a 5'-nucleotide monophosphate, comprising 5'-adenosinic acid (AMP), 5'-inosinic acid (IMP) or a physiologically acceptable salt thereof wherein said taurine and said 5'-nucleotide monophosphate are present in an amount effective to reduce the bitter taste of said potassium chloride, and wherein said composition is not seafood and is not an extract of seafood.

2. A composition according to claim 1, wherein said 5'-nucleotide monophosphate comprises AMP or a physiologically acceptable salt thereof.

3. A composition according to claim 2, wherein the amount of said AMP or physiologically acceptable salt thereof is between about 100 ppm and about 800 ppm w/w of said food or w/v of said beverage.

4. A composition according to claim 1, wherein said 5'-nucleotide monophosphate comprises IMP or a physiologically acceptable salt thereof.

5. A composition according to claim 4, wherein the amount of said IMP or physiologically acceptable salt thereof is up to about 600 ppm w/w of said food or w/v of said beverage.

6. A composition according to claim 1, wherein said 5'-nucleotide monophosphate comprises a combination of AMP and IMP, or physiologically acceptable salts thereof.

7. A composition according to claim 1, wherein said 5'-nucleotide monophosphate comprises a combination of AMP, IMP and 5'-guanylic acid (GMP), or physiologically acceptable salts thereof.

8. A composition according to claim 7, wherein the amount of said potassium chloride is about 0.9%, the amount of said taurine or physiologically acceptable salt thereof is about 750 ppm, the amount of said AMP or physiologically acceptable salt thereof is about 400 ppm, the amount of said IMP or physiologically acceptable salt thereof is about 100 ppm, and the amount of said GMP or physiologically acceptable salt thereof is about 100 ppm, w/w of said food or w/v of said beverage.

9. A composition according to claim 7, wherein the amount of said potassium chloride is between about 0.5% and about 1.5%, the amount of said taurine or physiologically acceptable salt thereof is between about 400 ppm and about 750 ppm, the amount of said AMP or physiologically acceptable salt thereof is between about 100 ppm and about 800 ppm, the amount of said IMP or physiologically acceptable salt thereof is up to about 600 ppm and the amount of said GMP or physiologically acceptable salt thereof is up to about 600 ppm, w/w of said food or w/v of said beverage.

10. A composition according to claim 1, wherein said 5'-nucleotide monophosphate consists essentially of AMP, IMP, GMP, combinations thereof or physiologically acceptable salts thereof.

11. A composition according to claim 1, wherein the amount of said potassium chloride is about 0.9% w/w of said food or w/v of said beverage.

12. A composition according to claim 1, wherein the amount of said taurine or physiologically acceptable salt thereof is about 750 ppm w/w of said food or w/v of said beverage.

13. A composition according to claim 1, wherein the amount of said AMP or physiologically acceptable salt thereof is about 600 ppm w/w of said food or w/v of said beverage.

14. A composition according to claim 1, wherein the amount of said IMP or physiologically acceptable salt thereof is about 200 ppm w/w of said food or w/v of said beverage.

15. A composition according to claim 1, wherein the amount of said potassium chloride is between about 0.5% and about 1.5% w/w of said food or w/v of said beverage.

16. A composition according to claim 1, wherein the amount of said taurine or physiologically acceptable salt thereof is between about 400 ppm and about 1200 ppm w/w of said food or w/v of said beverage.

17. A composition according to claim 1, wherein said food or beverage is chicken broth.

18. A composition according to claim 1, wherein said food or beverage is beef gravy.

19. A method of reducing sodium intake and increasing potassium intake in the diet of an individual, comprising administering to said individual the composition of claim 1.

20. A method of preparing the composition of claim 1, comprising adding to said food or beverage (a) an amount of potassium chloride effective to induce a bitter taste and induce a salty taste, (b) an amount of taurine or physiologically acceptable salt thereof and (c) an amount of a 5'-nucleotide monophosphate wherein said 5'-nucleotide monophosphate comprises AMP, IMP or physiologically acceptable salts thereof, and wherein said amount of taurine and said amount of 5'-nucleotide monophosphate are effective to reduce the bitter taste of said potassium chloride.

21. The method of claim 20, wherein said 5'-nucleotide monophosphate comprises a combination of AMP and IMP, or physiologically acceptable salts thereof.

22. The method of claim 20, wherein said 5'-nucleotide monophosphate comprises a combination of AMP, IMP and GMP, or physiologically acceptable salts thereof.

23. A salt substitute consisting essentially of (a) potassium chloride, wherein said potassium chloride is present in an amount effective to induce a bitter taste and induce a salty taste, (b) taurine or physiologically acceptable salt thereof, and (c) a 5'-nucleotide monophosphate comprising AMP, IMP, or a physiologically acceptable salt thereof, wherein said taurine and said 5'-nucleotide monophosphate are present in an amount effective to reduce the bitter taste of said potassium chloride.

24. A salt substitute according to claim 23, wherein said 5'-nucleotide monophosphate comprises AMP or a physiologically acceptable salt thereof.

25. A salt substitute according to claim 23, wherein said 5'-nucleotide monophosphate comprises IMP or a physiologically acceptable salt thereof.

26. A salt substitute according to claim 25, wherein the amount of said IMP or physiologically acceptable salt thereof is up to about 4% w/w of said salt substitute.

27. A salt substitute according to claim 23, wherein said 5'-nucleotide monophosphate comprises a combination of AMP and IMP, or physiologically acceptable salts thereof.

28. A salt substitute according to claim 27, wherein the amount of said potassium chloride is about 86.95%, the amount of said taurine or physiologically acceptable salt thereof is about 7.25%, the amount of said AMP or physiologically acceptable salt thereof is about 3.86%, and the amount of said IMP or physiologically acceptable salt thereof is about 1.94%, w/w of said salt substitute.

29. A salt substitute according to claim 23, wherein said 5'-nucleotide monophosphate comprises a combination of AMP, IMP and GMP, or physiologically acceptable salts thereof.

30. A salt substitute according to claim 29, wherein the amount of said potassium chloride is about 86.95%, the amount of said taurine or physiologically acceptable salt thereof is about 7.25%, the amount of said AMP or physiologically acceptable salt thereof is about 3.86%, the amount of said IMP or physiologically acceptable salt thereof is about 0.97% and the amount of said GMP or physiologically acceptable salt thereof is about 0.97%, w/w of said salt substitute.

31. A salt substitute according to claim 23, wherein said 5'-nucleotide monophosphate consists essentially of AMP, IMP, GMP, combinations thereof or physiologically acceptable salts thereof.

32. A salt substitute according to claim 23, wherein the amount of said potassium chloride is between about 80% and about 98% w/w of said salt substitute.

33. A salt substitute according to claim 23, wherein the amount of said taurine or physiologically acceptable salt thereof is between about 2% and about 15% w/w of said salt substitute.

34. A salt substitute according to claim 24, wherein the amount of said AMP or physiologically acceptable salt thereof is between about 1% and about 8% w/w of said salt substitute.

35. A salt substitute according to claim 23, wherein the amount of GMP or physiologically acceptable salt thereof is up to about 4% w/w of said salt substitute.

36. A method of reducing sodium intake and increasing potassium intake in the diet of an individual, comprising administering to said individual the composition of claim 23.

37. A method of preparing the salt substitute of claim 23, comprising mixing (a) an amount of potassium chloride effective to induce a bitter taste, (b) an amount of taurine or physiologically acceptable salt thereof, and (c) an amount of a 5'-nucleotide monophosphate wherein said 5'-mononucleotide monophosphate comprises AMP, IMP or a physiologically acceptable salt thereof, and wherein said amount of taurine and said amount of 5'-nucleotide monophosphate are effective to reduce the bitter taste of said potassium chloride.

38. The method of claim 37, wherein said 5'-nucleotide monophosphate comprises a combination of AMP and IMP, or physiologically acceptable salts thereof.

39. The method of claim 37, wherein said 5'-nucleotide monophosphate comprises a combination of AMP, IMP and GMP, or physiologically acceptable salts thereof.

40. A composition comprising tastands consisting essentially of (a) taurine or physiologically acceptable salt thereof, and (b) a 5'-nucleotide monophosphate selected from the group consisting of AMP, IMP, combinations of AMP and IMP, combinations of AMP, IMP and GMP, and physiologically acceptable salts thereof, wherein said tastands are present in an amount effective to reduce a bitter taste of potassium chloride.

41. A composition according to claim 40, wherein said 5'-nucleotide monophosphate is AMP or a physiologically acceptable salt thereof.

42. A composition according to claim 40, wherein said 5'-nucleotide monophosphate is IMP or a physiologically acceptable salt thereof.

43. A composition according to claim 40, wherein said 5'-nucleotide monophosphate is a combination of AMP and IMP, or physiologically acceptable salts thereof.

44. A composition according to claim 40, wherein said 5'-nucleotide monophosphate is a combination of AMP, IMP and GMP, or physiologically acceptable salts thereof.

45. A composition according to claim 40, wherein said taurine or physiologically acceptable salt thereof is between about 40% and about 80% w/w of said tastands.

46. A method of reducing sodium intake and increasing potassium intake in the diet of an individual, comprising administering to said individual the composition of claim 40.

47. A method of preparing the composition of claim 40, comprising mixing (a) an amount of taurine or physiologically acceptable salt thereof, and (b) a 5'-nucleotide monophosphate selected from the group consisting of AMP, IMP, combinations of AMP and IMP, combinations of AMP, IMP and GMP, and physiologically acceptable salts thereof, and wherein said amount of taurine and said amount of 5'-nucleotide monophosphate are effective to reduce a bitter taste of potassium chloride.

48. The method of claim 47, wherein said 5'-nucleotide monophosphate comprises a combination of AMP, IMP and GMP, or physiologically acceptable salts thereof. monophosphate comprises a combination of AMP and IMP, or 49. The method of claim 47, wherein said 5'-nucleotide physiologically acceptable salts thereof.

* * * * *

UNITED STATES PATENT AND TRADEMARK OFFICE
CERTIFICATE OF CORRECTION

PATENT NO. : 7,455,872 B2
APPLICATION NO. : 11/155745
DATED : November 25, 2008
INVENTOR(S) : Salemme et al.

It is certified that error appears in the above-identified patent and that said Letters Patent is hereby corrected as shown below:

In claim 1, column 14, line 37, please insert a --,-- after the word "thereof.".

In claim 24, column 16, line 4, please delete "said5'-" and replace it with "said 5'-".

In claim 25, column 16, line 7, please delete "said5'-" and replace it with "said 5'-".

In claim 27, column 16, line 13, please delete "said5'-" and replace it with "said 5'-".

In claim 29, column 16, line 23, please delete "said5'-" and replace it with "said 5'-".

In claim 31, column 16, line 35, please delete "said5'-" and replace it with "said 5'-".

In claim 41, column 16, line 12, please delete "said5'-" and replace it with "said 5'-".

In claim 42, column 16, line 15, please delete "said5'-" and replace it with "said 5'-".

In claim 43, column 16, line 18, please delete "said5 '-" and replace it with "said 5'-".

In claim 44, column 16, line 21, please delete "said5'-" and replace it with "said 5'-".

In claim 48, column 18, lines 18-19, please delete "monophosphate comprises a combination of AMP and IMP, or".

UNITED STATES PATENT AND TRADEMARK OFFICE
CERTIFICATE OF CORRECTION

PATENT NO. : 7,455,872 B2
APPLICATION NO. : 11/155745
DATED : November 25, 2008
INVENTOR(S) : Salemme et al.

It is certified that error appears in the above-identified patent and that said Letters Patent is hereby corrected as shown below:

In claim 49, column 18, lines 20-21, please insert --monophosphate comprises a combination of AMP and IMP, or-- after the word "nucleotide" and before the word "physiologically.".

Signed and Sealed this

Thirty-first Day of March, 2009

JOHN DOLL
*Acting Director of the United States Patent and Trademark Office*